US011179393B2

(12) United States Patent
Visco

(10) Patent No.: US 11,179,393 B2
(45) Date of Patent: Nov. 23, 2021

(54) METHODS OF TREATING OR PREVENTING PRETERM LABOR

(71) Applicant: Anthony G. Visco, Chapel Hill, NC (US)

(72) Inventor: Anthony G. Visco, Chapel Hill, NC (US)

(*) Notice: Subject to any disclaimer, the term of this patent is extended or adjusted under 35 U.S.C. 154(b) by 0 days.

(21) Appl. No.: 16/431,148

(22) Filed: Jun. 4, 2019

(65) Prior Publication Data
US 2020/0121683 A1    Apr. 23, 2020

Related U.S. Application Data

(63) Continuation of application No. 15/308,510, filed as application No. PCT/US2015/029455 on May 6, 2015, now abandoned.

(60) Provisional application No. 61/989,221, filed on May 6, 2014.

(51) Int. Cl.
| A61K 31/215 | (2006.01) |
| A61K 31/216 | (2006.01) |
| A61K 31/135 | (2006.01) |
| A61P 15/06 | (2006.01) |
| A61K 31/517 | (2006.01) |
| A61K 31/46 | (2006.01) |
| A61K 31/137 | (2006.01) |
| A61K 31/196 | (2006.01) |
| A61K 31/4025 | (2006.01) |
| A61K 31/439 | (2006.01) |
| A61K 31/4439 | (2006.01) |
| A61K 31/445 | (2006.01) |
| A61K 31/4525 | (2006.01) |
| A61K 31/4725 | (2006.01) |
| A61K 31/222 | (2006.01) |
| A61K 31/36 | (2006.01) |
| A61K 31/4465 | (2006.01) |
| A61K 31/145 | (2006.01) |
| A61K 31/357 | (2006.01) |
| A61K 31/426 | (2006.01) |

(52) U.S. Cl.
CPC .......... *A61K 31/517* (2013.01); *A61K 31/135* (2013.01); *A61K 31/137* (2013.01); *A61K 31/145* (2013.01); *A61K 31/196* (2013.01); *A61K 31/215* (2013.01); *A61K 31/216* (2013.01); *A61K 31/222* (2013.01); *A61K 31/357* (2013.01); *A61K 31/36* (2013.01); *A61K 31/4025* (2013.01); *A61K 31/426* (2013.01); *A61K 31/439* (2013.01); *A61K 31/445* (2013.01); *A61K 31/4439* (2013.01); *A61K 31/4465* (2013.01); *A61K 31/4525* (2013.01); *A61K 31/46* (2013.01); *A61K 31/4725* (2013.01); *A61P 15/06* (2018.01)

(58) Field of Classification Search
CPC .. A61K 31/135; A61K 31/137; A61K 31/145; A61K 31/196; A61K 31/215; A61K 31/216; A61K 31/222; A61K 31/357; A61K 31/36; A61K 31/4025; A61K 31/426; A61K 31/439; A61K 31/4439; A61K 31/445; A61K 31/4465; A61K 31/4525; A61K 31/46; A61K 31/4725; A61K 31/517; A61P 15/06
See application file for complete search history.

(56) References Cited

U.S. PATENT DOCUMENTS

| 5,516,702 | A | 5/1996 | Senyei et al. |
| 5,708,036 | A | 1/1998 | Pesterfield, Jr. |
| 5,872,126 | A | 2/1999 | Cukierski et al. |
| 6,017,927 | A | 1/2000 | Takeuchi et al. |
| 6,207,852 | B1 | 3/2001 | Aberg et al. |
| 6,310,050 | B1 | 10/2001 | Advenier et al. |
| 7,141,696 | B2 | 11/2006 | Aberg et al. |
| 7,723,356 | B2 * | 5/2010 | Press ............... A61P 11/16 |
| | | | 514/305 |
| 2007/0167992 | A1 | 7/2007 | Carley |

(Continued)

FOREIGN PATENT DOCUMENTS

| EP | 2 386 555 A1 | 11/2011 |
| EP | 2 592 078 A1 | 5/2013 |

(Continued)

OTHER PUBLICATIONS

Jirschele et. al., Int. Urogynecol. J., Sep. 14, 2012, The Int Urogynecol. Assoc., vol. 24, pp. 595-604 (Year: 2012).*

(Continued)

*Primary Examiner* — Sarah Pihonak
(74) *Attorney, Agent, or Firm* — Foley Hoag LLP

(57) ABSTRACT

Described herein are methods for treating preterm labor, stopping labor prior to Cesarean delivery, preventing preterm labor, or controlling the timing of parturition by administering a chemical compound, such as a muscarinic receptor antagonist preferably a M, receptor antagonist, or a β-3 adrenergic agonist. Also described are methods for treating preterm labor, stopping labor preparatory to Cesarean delivers', preventing preterm labor, or controlling the timing of parturition by administering an effective amount of transdermal stimulation, posterior tibial nerve stimulation or another form of non-invasive or invasive neuromodulation, unstimulated or stimulated acupuncture, magnetic field therapy, or vibratory stimulation. These methods may be practiced individually, in combination with each other, or in combination with known tocolytic methods or medications.

4 Claims, No Drawings

(56) References Cited

U.S. PATENT DOCUMENTS

| | | | |
|---|---|---|---|
| 2009/0062326 A1 | 3/2009 | Spindel et al. | |
| 2010/0190771 A1* | 7/2010 | Claffey | A61P 25/18 514/210.21 |
| 2011/0135580 A1 | 6/2011 | Konetzki | |
| 2011/0312986 A1 | 12/2011 | Oefelein | |
| 2012/0082626 A1 | 4/2012 | Tan | |

FOREIGN PATENT DOCUMENTS

| | | | | |
|---|---|---|---|---|
| WO | WO-1998/009632 A1 | | 3/1998 | |
| WO | WO-2009068876 A1 | | 6/2009 | |
| WO | WO-2010104986 A1 | * | 9/2010 | A61P 15/04 |

OTHER PUBLICATIONS

Gjerdingen, J. Amer. Board Fam. Pract., 1992, vol. 5(5), pp. 495-509 (Year: 1992).*

Tahara et. al., J. Chromatography A, publ. 1999, vol. 848, pp. 465-471 (Year: 1999).*

Campbell et. al., J. Applied Physiology, publ. 1955, vol. 7(4), pp. 365-366 (Year: 1955).*

Balais et al., "Antagonistic effects of trifluoperazine, imipramine, and chlorpromazine against acetylcholine-induced contractions in isolated rat uterus," Kexue, 18(2):97-100 (1997).

Campbell et al., "Absence of Effect of Bentyl Hydrochloride Upon Human Uterus During Parturition," Journal of Applied Physiology, 7:365-366 (1955).

CAS STN Abstract, Registry No. 320345-99-1, dated Feb. 6, 2001.

Edwards et al., "Reproductive toxicity studies with oxybutynin hydrochloride," Toxicology, 40(1): 31-44 (1986).

Extended European Search Report for EP Application No. 15788577.3 dated Feb. 5, 2018.

Fardiazar et al., "Hyoscine-N-butylbromide versus atropine as labour accelerant and analgesic: A randomized clinical trial," Journal of Biological Sciences, 16:443-445 (Abstract) (2013) [online] Retrieved from the Internet: doi:10.3923/pjbs.2013.443.445.

Garza et al., "*Clostridium Botulinum* Toxin Inhibits Myometrial Activity In Vitro: Possible Application on the Prevention of Preterm Labor After Fetal Surgery," Journal of Pediatric Surgery, 38(3):511-513 (2003).

Hegde et al., "Muscarinic receptor subtypes modulating smooth muscle contractility in the urinary bladder," Life Sci.;64(6-7):419-28 (1999).

International Search Report dated Aug. 27, 2015 from PCT/US2015/029455.

Kitazawa et al., "Muscarinic receptor subtypes involved in carbachol-induced contraction of mouse uterine smooth muscle," Naunyn Schmiedebergs Arch Pharmacol, 377(4-6): 503-513 (2008).

Kobayashi et al., "Effects of imidafenacin (KRP-197/ONO-8025), a new anti-cholinergic agent, on muscarinic acetylcholine receptors. High affinities for M3 and M1 receptor subtypes and selectivity for urinary bladder over salivary gland," Arzneimittelforschung; 57(2):92-100 (2007).

Manski, "Anatomy of the bladder," (2017). [http://www.urology-textbook.com/bladder-anatomy.html].

Meis et al., "Prevention of recurrent preterm delivery by 17 alpha-hydroxyprogesterone caproate," N Engl J Med, 348(24): 2379-2385 (2003).

Partial Supplementary European Search Report for European Application No. 15788577.3 dated Oct. 25, 2017.

Prescribing Information for Oxytrol (oxybutynin transdermal system), pp. 1-26, revised: Jul. 2015.

Prescribing Information for SANCTURA XR (trospium chloride extended release capsules), pp. 1-18, revised: Aug. 2012.

Prescribing Information for VESIcare (solifenacin succinate), pp. 1-19, revised: Feb. 2016.

Shaya et al., "Persistence with overactive bladder pharmacotherapy in a Medicaid population," Am J Manag Care, 11(4 Suppl): S121-S129 (2005).

Vernon et al., "Role of Muscarinic Acetylcholine Receptors in Pregnant Rat Uterine Cervical Ripening," (Abstract) [online] Retrieved on Aug. 13, 2015] Retrieved from the Internet: <URL: http://inspire.redlands.edu/cas_honors/50/>.

Visco et al., "Anticholinergic therapy vs. onabotulinumtoxinA for urgency urinary incontinence," N Engl J Med, 367(19): 1803-1813 (2012).

Crowther et al., "Magnesium sulphate for preventing preterm birth in threatened preterm labour," Cochrane Database of Systematic Reviews, Issue 4, 2002.

* cited by examiner

METHODS OF TREATING OR PREVENTING PRETERM LABOR

RELATED APPLICATIONS

This application is a continuation of U.S. patent application Ser. No. 13/308,510, filed Nov. 2, 2016, which is the United States National Stage application of PCT/US2015/029455, filed May 6, 2015, which claims the benefit of priority to U.S. Provisional Patent Application Ser. No. 61/989,221, filed May 6, 2014, each of which is hereby incorporated by reference in its entirety.

BACKGROUND

In the field of obstetrics, one of the most important problems is the management of preterm labor. A significant number of the pregnancies progressing past 20 weeks of gestation experience premature labor and delivery, which are leading causes of neonatal morbidity and mortality. In addition, surviving pre-term babies suffer from long-term sequelae, such as neurologic deficits, blindness, deafness, and chronic respiratory disease. Despite major advances in neonatal care, retention of the fetus in utero is preferred in most instances.

Currently, pre-term labor is treated with tocolytic (uterine-relaxing) agents, including β2-adrenergic agonists, magnesium sulfate, and ethanol. In addition, oxytocin receptor antagonists are in development. Ritodrine, the leading β2-adrenergic agonist, causes a number of cardiovascular and metabolic side effects in the mother, including tachycardia, increased renin secretion, and hyperglycemia (and reactive hypoglycemia in the infant). Ritodrine is no longer FDA-approved. Other β2-adrenergic agonists, including salbutamol, terbutaline, and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression, and cardiac arrest, thus making this agent unsuitable when renal function is impaired. Ethanol is as effective as ritodrine in preventing premature labor, but it docs not produce a corresponding reduction in the incidence of fetal respiratory distress that administration of ritodrine does. Progesterone has also been shown to reduce preterm delivery, but its mechanism of action is unclear.

There exists a need for safe and effective methods of treating or preventing preterm labor.

SUMMARY

In certain embodiments, the invention relates to a method for treating preterm labor, stopping labor preparatory to Cesarean delivery, preventing preterm labor, or controlling the timing of parturition comprising the step of:
administering to a patient in need thereof an effective amount of a muscarinic antagonist.

In certain embodiments, the invention relates to any of the methods described herein, wherein the muscarinic antagonist has high selectivity for the $M_3$ receptor compared with the $M_2$ receptor.

In certain embodiments, the invention relates to any of the methods described herein, wherein the muscarinic antagonist has high affinity for the $M_3$ receptor.

In certain embodiments, the invention relates to any of the methods described herein, wherein the muscarinic antagonist is selected from the group consisting of (3R,2'R)-1-azabicyclo[2.2.2]octan-8-yl 2-cyclopentyl-2-hydroxy-2-phenylethanoate, ((3R)-1-[2-(1-,3-benzodioxol-5-yl)ethyl]-3-(diphenylmethoxy)piperidine (Zamifenacin), (aR)-a-cyclopentyl-a-hydroxy-N-[1-(4-methyl-3-pentenyl)-4-piperidinyl]benzenacetamide, darifenacin, dicycloverine, a 1,1-dimethyl-4-diphenylacetoxypiperidinium salt (such as a halide salt, for example, iodide), fesoterodine, 5-hydroxymethyltolterodine, hyoscyamine, ipratropium, 8-methyl-8-azabicyclo-3-endo[1.2.3]oct-3-yl-1,4-dihydro-2-oxo-3(2H)-quinazolinecarboxylic acid ester, oxybutynin, propiverine, solifenacin, temiverine, a tiotropium salt (such as a halide salt, for example, bromide), and trospium.

In certain embodiments, the invention relates a method for treating preterm labor, stopping labor preparatory to Cesarean delivery, preventing preterm labor, or controlling the timing of parturition comprising the step of:
administering to a patient in need thereof an effective amount of transdermal stimulation, posterior tibial nerve stimulation or another form of non-invasive or invasive neuromodulation, unstimulated or stimulated acupuncture, magnetic field therapy, or vibratory stimulation.

In certain embodiments, the invention relates to a pharmaceutical composition for treating preterm labor, stopping labor preparatory to Cesarean delivery, preventing preterm labor, or controlling the timing of parturition comprising a therapeutically-effective amount of a muscarinic antagonist and a pharmaceutically acceptable carrier and/or diluent.

DETAILED DESCRIPTION

Overview

The human bladder (urinary system) and the uterus (genital system) originate from the same embryologic origin (i.e., intermediate mesoderm). The anatomy of the bladder and the uterus are similar: both are hollow, smooth muscle organs found in the pelvis; both have two inlets and one outlet; and both have the same blood supply (i.e., internal iliac). Also, there is evidence that the innervation of the bladder and the innervation of the uterus share some commonality: both receive the majority of parasympathetic innervation via the pelvic nerve; both receive the majority of the sympathetic innervation from the hypogastric plexus; both have muscarinic receptors, predominately M2 and M3; and the M3 receptor is the dominant (most important) receptor in both the bladder and the uterus.

As such, treatments typically explored and used for bladder dysfunction such as overactive bladder, urgency, frequency, urge incontinence, and urgency urinary incontinence may be used to treat or prevent uterine contractions, preterm labor, and preterm delivery. These therapies generally reduce or block acetylcholine release, block or inactivate muscarinic receptors, block or inactivate acetylcholine receptors, stimulate beta receptors (such as beta-2 or beta-3), or reduce parasympathetic output.

In certain embodiments, the invention provides for a method of treating preterm labor, a method for stopping labor preparatory (i.e., prior) to Cesarean delivery, a method for preventing preterm labor, and a method of controlling the timing of parturition. In certain embodiments, the invention provides for a method of manufacture of a medicament useful for treating preterm labor and for stopping labor preparatory to Cesarean delivery, and for pharmaceutical compositions useful in the methods of treating and preventing preterm labor, stopping labor prior to Cesarean delivery and controlling the timing of parturition.

In certain embodiments, aspects of the invention are described in U.S. Pat. Nos. 5,708,036, 5,872,126, 6,017,927, 6,207,852, and 7,141,696, and U.S. Published Patent Application Publication Nos. 2007/0167992, 2009/0270452, 2011/312986, 2012/0301540, 2013/072746, and 2013/296588, each of which is hereby incorporated by reference in its entirety.

Definitions

As used herein, the articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A. and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "Cesarean delivery" shall mean incision through the abdominal and uterine walls for delivery of a fetus.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of condition, stabilized (i.e., not worsening) state of condition, delay or slowing of progression of condition, amelioration or palliation of the state of condition, and remission (whether partial or total), whether detectable or undetectable.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" refers to a mammal in need of a particular treatment. In certain embodiments, a patient is a primate, canine, feline, or equine. In certain embodiments, a patient is a human.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water, (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.)

In other cases, the compounds useful in the methods of the invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

Exemplary Methods

In certain embodiments, the invention provides for a method of treating preterm labor, a method for stopping labor preparatory (i.e., prior) to Cesarean delivery, a method for preventing preterm labor, and a method of controlling the timing of parturition. In certain embodiments, the invention provides for a method of manufacture of a medicament useful for treating preterm labor and for stopping labor preparatory to Cesarean delivery, and for pharmaceutical compositions useful in the methods of treating and preventing preterm labor, stopping labor prior to Cesarean delivery and controlling the timing of parturition.

In certain embodiments, the invention relates to any one of the aforementioned methods, wherein delivery or parturition is delayed or prevented for at least about 2 days, at least about 3 days, at least about 4 days, at least about 5 days, at least about 6 days, at least about 7 days, at least about 8 days, at least about 9 days, or at least about 10 days. In certain embodiments, the invention relates to any one of the aforementioned methods, wherein delivery or parturition is delayed or prevented until the fetus is at about 40 weeks gestational age, about 39 weeks, about 38 weeks, or about 37 weeks gestational age.

In certain embodiments, the invention relates to any one of the aforementioned methods, comprising the step of administering to a patient in need thereof an effective amount of a compound. In certain embodiments, the compound is an anticholinergic compound. In certain embodiments, the compound is a muscarinic antagonist. Muscarinic antagonists bind to, but do not activate, muscarinic cholinergic receptors. Rather, they act by blocking the action of endogenous acetylcholine, a neurotransmitter found in both peripheral and central nervous systems. In certain embodiments, the compound for use in the invention has high selectivity for the $M_3$ receptor compared with the $M_2$ receptor. In certain embodiments, the compound for use in the invention has high affinity for the $M_3$ receptor.

Compounds having muscarinic receptor antagonistic activities cause bronchodilation, suppression of gastrointestinal motility, suppression of acid secretion, dry mouth, mydriasis, suppression of bladder contraction, hypohidrosis, tachycardia, or the like. The muscarinic receptor includes at least three subtypes. The $M_1$ receptor mainly exists in the brain or the like, the $M_2$ receptor in the heart or the like, and the $M_3$ receptor in the smooth muscles or gland tissues.

A number of compounds having muscarinic receptor antagonistic activities are known; for example, atropine is a typical example. However, atropine antagonizes the $M_1$, $M_2$ and $M_3$ receptors non-selectively, so that it is difficult to use it for the treatment of a specific disease. In recent years, according to the progress of the studies on the subtypes of the muscarinic receptor, compounds having selective antagonistic activities against the $M_1$, $M_2$, or $M_3$ receptor have been investigated. In certain embodiments, the invention relates to the use of a compound having selective antagonistic activity against muscarinic $M_3$ receptor that is free from the cardiac side effects resulting from the $M_2$ receptor.

In certain embodiments, the compounds used in the inventive methods have affinity and selectivity for the muscarinic $M_3$ receptor and, as an $M_3$ receptor antagonist, are useful as agents for prevention or treatment of various $M_3$ receptor-related diseases.

In particular, in certain embodiments, the compounds useful in the methods described herein have high selectivity for the $M_3$ receptor existing in the smooth muscle or gland tissues compared with the $M_2$ receptor existing in the heart, so that they have high utility as $M_3$ receptor antagonists having less side effects on the heart. In certain embodiments, these compounds show good muscarinic $M_3$ antagonistic activity but low activity on bradycardia. In certain embodiments, these compounds have fewer side effects, such as dry mouth, compared with the conventional anti-cholinergic agents.

In certain embodiments, the compounds used in the inventive methods have affinity and selectivity for the muscarinic $M_2$ receptor and, as an $M_2$ receptor antagonist, are useful as agents for prevention or treatment of various $M_2$ receptor-related diseases.

In particular, in certain embodiments, the compounds useful in the methods described herein have high selectivity for the $M_2$ receptor. In certain embodiments, these compounds show good muscarinic $M_2$ antagonistic activity. In certain embodiments, these compounds have fewer side effects, such as dry mouth, compared with the conventional anti-cholinergic agents.

In certain embodiments, the invention relates to any one of the aforementioned methods, wherein the compound is selected from the group consisting of (3R,2'R)-1-azabicyclo[2.2.2]octan-8-yl 2-cyclopentyl-2-hydroxy-2-phenylethanoate, ((3R)-1-[2-(1-,3-benzodioxol-5-yl)ethyl]-3-(diphenylmethoxy)piperidine (Zamifenacin), (aR)-a-cyclopentyl-a-hydroxy-N-[1-(4-methyl-3-pentenyl)-4-piperidinyl] benzeneacetamide, darifenacin, dicycloverine, a 1,1-dimethyl-4-diphenylacetoxypiperidinium salt (such as a halide salt, for example, iodide), fesoterodine, 5-hydroxymethyltolterodine, hyoscyamine, ipratropium, 8-methyl-8-azabicyclo-3-endo[1.2.3]oct-3-yl-1,4-dihydro-2-oxo-3(2H)-quinazolinecarboxylic acid ester, mirabegron, oxybutynin, propiverine, solifenacin, temiverine, a tiotropium salt (such as a halide salt, for example, bromide), trospium, a smooth muscle spasmolytic agent, a beta-2 agonist, and a beta-3 agonist (e.g., mirabegron).

In certain embodiments, the invention relates to any one of the aforementioned methods, wherein the compound is selected from the group consisting of darifenacin, dicycloverine, fesoterodine, 5-hydroxymethyltolterodine, ipratropium, mirabegron, oxybutynin, propiverine, solifenacin, temiverine, trospium, a smooth muscle spasmolytic agent, a beta-2 agonist, and a beta-3 agonist (e.g., mirabegron).

In certain embodiments, the invention relates to any one of the aforementioned methods, wherein the compound is selected from the group consisting of dicycloverine, 5-hydroxymethyltolterodine, ipratropium, mirabegron, propiverine, solifenacin, a beta-2 agonist, and a beta-3 agonist (e.g., mirabegron).

In certain embodiments, the invention relates to any one of the aforementioned methods, wherein the compound is tolterodine.

In certain embodiments, the invention relates to any one of the aforementioned methods, wherein the compound is not tolterodine.

In certain embodiments, the invention relates to any one of the aforementioned methods, wherein the compound is a compound of Formula I:

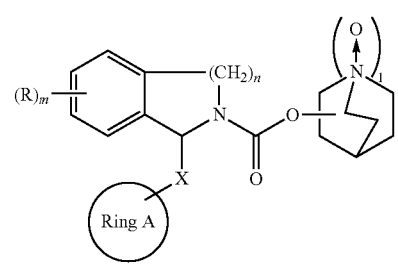

Formula I or a pharmaceutically acceptable salt thereof,
wherein, independently for each occurrence,
Ring A is an aryl group, a cycloalkyl group, a cycloalkenyl group, a heteroaryl group having 1 to 4 hetero atoms selected from the group consisting of an oxygen atom, a nitrogen atom and a sulfur atom or a 5- to 7-membered saturated heterocyclic group, wherein said ring may be substituted by an optional substituent;

X is a single bond or a methylene group;

R is a halogen atom, a hydroxyl group, a lower alkoxy group, a carboxyl group, a lower alkoxycarbonyl group, a lower acyl group, a mercapto group, a lower alkylthio group, a sulfonyl group, a lower alkylsulfonyl group, a sulfinyl group, a lower alkylsulfinyl group, a sulfonamido group, a lower alkanesulfonamido group, a carbamoyl group, a thiocarbamoyl group, a mono- or di-lower alkylcarbamoyl group, a nitro group, a cyano group, an amino group, a mono- or di-lower alkylamino group, a methylenedioxy group, an ethylenedioxy group or a lower alkyl group which may be substituted by a halogen atom, a hydroxyl group, a lower alkoxy group, an amino group or a mono- or di-lower alkylamino group;

l is 0 or 1,
m is 0, 1, 2, or 3, and
n is 1 or 2.

Examples of compounds of Formula I may be found in the tables of U.S. Pat. No. 6,017,927, which is hereby incorporated by reference in its entirety.

In certain embodiments, the invention relates to any one of the aforementioned methods, wherein the compound is a compound of Formula II:

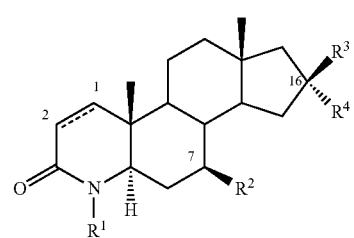

Formula II or a pharmaceutically acceptable salt thereof,
wherein, independently for each occurrence,
the C1-C2 carbon-carbon bond may be a single bond, or a double bond as indicated by the dashed line;
$R^1$ is hydrogen or C1-10 alkyl;
$R^2$ is hydrogen or C1-10 alkyl; and
$R^3$ and $R^4$ are defined as in WO 1998/009632, which is hereby incorporated by reference in its entirety.

In certain embodiments, the invention relates to any one of the aforementioned methods, wherein any of the compounds described herein, such as a muscarinic receptor antagonist, is co-administered with magnesium. In certain embodiments, the invention relates to any one of the aforementioned methods, wherein any of the compounds described herein is co-administered with a steroid, such as progesterone. In certain embodiments, the invention relates to any one of the aforementioned methods, wherein any of the compounds described herein is co-administered with a second, different compound described herein.

In certain embodiments, the invention relates to any one of the aforementioned methods, comprising the step of administering to a patient in need thereof an effective amount of transdermal stimulation, posterior tibial nerve stimulation or another form of non-invasive or invasive neuromodulation, unstimulated or stimulated acupuncture, magnetic field therapy, or vibratory stimulation.

In certain embodiments, the invention relates to any one of the aforementioned methods, wherein transdermal stimulation, posterior tibial nerve stimulation or another form of non-invasive or invasive neuromodulation, unstimulated or stimulated acupuncture, magnetic field therapy, or vibratory stimulation is co-administered with a compound described herein, such as a muscarinic receptor antagonist, magnesium, or a steroid, such as progesterone. In certain embodiments, the invention relates to any one of the aforementioned methods, wherein one kind of transdermal stimulation, posterior tibial nerve stimulation or another form of non-invasive or invasive neuromodulation, unstimulated or stimulated acupuncture, magnetic field therapy, or vibratory stimulation is co-administered with a second kind of transdermal stimulation, posterior tibial nerve stimulation or another form of non-invasive or invasive neuromodulation, unstimulated or stimulated acupuncture, magnetic field therapy, or vibratory stimulation.

In certain embodiments, the invention relates to any one of the aforementioned methods, comprising the step of administering to a patient in need thereof an effective amount of transdermal stimulation. In certain embodiments, the invention relates to any one of the aforementioned methods, comprising the step of administering to a patient in need thereof an effective amount of posterior tibial nerve stimulation. Generally, electrical energy has been applied to the nerves in the art for many years in an effort to control chronic pain control; however, the interaction of the electrical energy and the tissue of the nervous system is not fully understood and therefore has limited its use in many areas. Many of the devices in the art use neuromodulation systems to mask pain, rather than control labor contractions. Generally, the electrodes may be a percutaneous electrode or other electrode known to the skilled artisan. The percutaneous electrode requires a less-invasive implantation method and allows the positioning of multiple electrodes into the tissue to create an array of electrodes as needed, but the electrodes are prone to migration. The one or more implantable electrodes may be individually a wire, a rod, a filament, a ribbon, a cord, a tube, a formed wire, a needle, a flat strip or combinations thereof. The one or more implantable electrodes may be held in position using any method known to the skilled artisan, including but not limited to stitches, epoxy, tape, glue, sutures or a combination thereof.

In certain embodiments, the invention relates to any one of the aforementioned methods, wherein an electrical energy generator is used to generate one or more electrical pulses in electrical communication with the one or more electrodes. The electrical pulses of the electrodes modulate labor and uterine contractions, or reduce the pain and/or discomfort associated with labor and uterine contractions. The electrical energy generator controls the pulse waveform, the signal pulse width, the signal pulse frequency, the signal pulse phase, the signal pulse polarity, the signal pulse amplitude, the signal pulse intensity, the signal pulse duration and combinations thereof of the one or more electrical pulses. The electrical energy generator may be used to convey a variety of currents and voltages to the one or more implantable electrodes to affect the nerves. The electrical energy generator may be used to control numerous electrodes independently or in various combinations as needed to provide stimulation. The skilled artisan will know the applicable ranges.

In certain embodiments, the invention relates to any one of the aforementioned methods, comprising the step of administering to a patient in need thereof an effective amount of botulinum toxin (BoNT).

In certain embodiments, the invention relates to any one of the aforementioned methods, wherein the compound is administered as a liposome. In certain embodiments, liposomes are used for intravesical drug delivery, especially delivery of BoNT. In certain embodiments, the use of liposomes allows a lower dose of the compound to be effective.

In certain embodiments, the invention relates to any one of the aforementioned methods, wherein the patient in need thereof is a human woman pregnant with a fetus at less than 40 weeks gestational age. In certain embodiments, the invention relates to any one of the aforementioned methods, wherein the patient in need thereof is a pregnant woman at 39 weeks, 38 weeks, 37 weeks, 36 weeks, 35 weeks, 34 weeks, 33 weeks, 32 weeks, 31 weeks, 30 weeks, 29 weeks, 28 weeks, 27 weeks, 26 weeks, 25 weeks, 24 weeks, 23 weeks, 22 weeks, 21 weeks, or 20 weeks gestational age.

In certain embodiments, the invention relates to any one of the aforementioned methods, wherein the patient in need thereof is a woman (i.e., a human woman) pregnant with a fetus weighing less than about 2500 g, less than about 2400 g, less than about 2300 g, less than about 2200 g, less than about 2100 g, or less than about 2000 g.

In certain embodiments, the invention relates to any one of the aforementioned methods, wherein the patient in need thereof is a pregnant woman whose cervix is dilated less than about 4 cm, less than about 3 cm, or less than about 2 cm.

In certain embodiments, the invention relates to any one of the aforementioned methods, wherein the patient in need thereof is a woman pregnant with a fetus who is not suffering from fetal distress, which is indicated by, for example, decreased fetal movement, or increased or decreased fetal heart rate.

In certain embodiments, the invention relates to any one of the aforementioned methods, wherein the patient in need thereof is a pregnant woman who smokes cigarettes. In certain embodiments, the invention relates to any one of the aforementioned methods, wherein the patient in need thereof is a pregnant woman who smoked cigarettes prior to conception.

In certain embodiments, the invention relates to any one of the aforementioned methods, wherein the patient in need thereof is a pregnant woman who was overweight or obese prior to conception.

In certain embodiments, the invention relates to any one of the aforementioned methods, wherein the patient in need thereof is a pregnant woman who was underweight prior to conception.

In certain embodiments, the invention relates to any one of the aforementioned methods, wherein the patient in need thereof is a pregnant woman with limited access to prenatal care.

In certain embodiments, the invention relates to any one of the aforementioned methods, wherein the patient in need thereof is a pregnant woman who drinks alcohol during her pregnancy.

In certain embodiments, the invention relates to any one of the aforementioned methods, wherein the patient in need thereof is a pregnant woman who uses illegal drugs during her pregnancy. In certain embodiments, the invention relates to any one of the aforementioned methods, wherein the patient in need thereof is a pregnant woman who uses cocaine during her pregnancy.

In certain embodiments, the invention relates to any one of the aforementioned methods, wherein the patient in need thereof is a pregnant woman also suffering from high blood pressure, preeclampsia, diabetes, a blood clotting disorder, placenta previa, placental abruption, cervical insufficiency, or an infection, such as *Chlamydia*, gonorrhea, trichomoniasis, kidney infection, pneumonia, appendicitis, asymptomatic bacteriuria, or bacterial vaginosis.

In certain embodiments, the invention relates to any one of the aforementioned methods, wherein the patient in need thereof is a pregnant woman who has underwent surgical fetal intervention or will undergo surgical fetal intervention.

In certain embodiments, the invention relates to any one of the aforementioned methods, wherein the patient in need thereof is a pregnant woman who is under 17 years of age.

In certain embodiments, the invention relates to any one of the aforementioned methods, wherein the patient in need thereof is a pregnant woman who is over 35 years of age. In certain embodiments, the invention relates to any one of the aforementioned methods, wherein the patient in need thereof is a pregnant woman who is over 40 years of age.

In certain embodiments, the invention relates to any one of the aforementioned methods, wherein the patient in need thereof is a pregnant woman who is African American.

In certain embodiments, the invention relates to any one of the aforementioned methods, wherein the patient in need thereof is a pregnant woman who suffered from vaginal bleeding during the first or second trimester of her pregnancy.

In certain embodiments, the invention relates to any one of the aforementioned methods, wherein the patient in need thereof is a pregnant woman who suffered from anemia during the first or second trimester of her pregnancy.

In certain embodiments, the invention relates to any one of the aforementioned methods, wherein the patient in need thereof is a pregnant woman who suffers from stress. In certain embodiments, the invention relates to any one of the aforementioned methods, wherein the patient in need thereof is a pregnant woman who suffers from chronic stress.

In certain embodiments, the invention relates to any one of the aforementioned methods, wherein the patient in need thereof is a pregnant woman who suffers from polyhydramnios.

In certain embodiments, the invention relates to any one of the aforementioned methods, wherein the patient in need thereof is a pregnant woman who conceived via in vitro fertilization.

In certain embodiments, the invention relates to any one of the aforementioned methods, wherein the patient in need thereof is a pregnant woman who is pregnant with twins or other multiples.

In certain embodiments, the invention relates to any one of the aforementioned methods, wherein the patient in need thereof is a pregnant woman who has a family history or a personal history of premature labor.

In certain embodiments, the invention relates to any one of the aforementioned methods, wherein the patient in need thereof is a pregnant woman who conceived less than 14 months, less than 13 months, less than 12 months, less than 11 months, less than 10 months, less than 9 months, less than 8 months, less than 7 months, less than 6 months, less than 5 months, less than 4 months, less than 3 months, less than 2 months, or less than 1 month after giving birth to a previous child. In certain embodiments, the invention relates to any one of the aforementioned methods, wherein the patient in need thereof is a pregnant woman who conceived less than 6 months, less than 5 months, less than 4 months, less than 3 months, less than 2 months, or less than 1 month after giving birth to a previous child.

In certain embodiments, the invention relates to any one of the aforementioned methods, wherein the patient in need thereof is a pregnant woman who is not also suffering from urinary incontinence.

In certain embodiments, the dosage of the active agents will generally be dependent upon a number of factors including pharmacodynamic characteristics of the agent, mode and route of administration of active agent(s), the health of the patient being treated, the extent of treatment desired, the nature and kind of concurrent therapy, if any, and the frequency of treatment and the nature of the effect desired. In general, dosage ranges of the active agents often range from about 0.001 to about 250 mg/kg body weight per day. For a normal adult having a body weight of about 70 kg, a dosage may range from about 0.1 to about 25 mg/kg body weight. However, some variability in this general dosage range may be required depending upon the age and weight of the subject being treated, the intended route of administration, the particular agent being administered and the like. Importantly, the determination of dosage ranges and optimal dosages for a particular mammal is also well within the ability of one of ordinary skill in the art having the benefit of the instant disclosure.

For example, a formulation intended for oral administration to humans may contain from about 0.1 mg to about 5 g of the therapeutic agent, which is compounded with an appropriate and convenient amount of carrier material varying from about 5 to about 95 percent of the total composition. Unit dosages will generally contain between about 0.5 mg to about 1500 mg of the therapeutic agent. In certain embodiments, the dosage is about 25 mg, 50 mg, 100 mg, 200 mg, 300 mg, 400 mg, 500 mg, 600 mg, 800 mg, or 1000 mg, etc., up to about 1500 mg of the therapeutic agent.

Dosage amount and interval may be adjusted on an individual or group basis to provide plasma levels of a particular active moiety or moieties sufficient to maintain the modulating effects or minimal effective concentration (MEC) of each of them. The MEC will vary for each compound and individual, but it can be estimated from in vitro data. Dosages necessary to achieve the MEC will depend on individual characteristics and route of administration. However, HPLC assays or bioassays can be used to determine plasma concentrations. In certain embodiments, the dose may be decreased. In certain embodiments, the dose may be increased.

Exemplary Pharmaceutical Compositions
Pharmaceutical Compositions/Formulations

The invention provides pharmaceutically acceptable compositions which comprise a therapeutically-effective amount of a compounds described above, formulated together with one or more pharmaceutically acceptable carriers (additives) and/or diluents. As described in detail below, the pharmaceutical compositions of the invention, or those used in the methods of the invention, may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin or intramurally; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a therapeutic agent in a composition of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (3) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (13) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the compounds found in the compositions may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds comprised in compositions of the invention. These salts can be prepared m situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the compounds that the compositions comprise include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like.

In other cases, the compounds comprised in compositions of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredients which can be combined with a carrier material to produce a single dosage form will vary depending upon the host being treated, the particular mode of administration. The amount of active ingredients which can be combined with a carrier material to produce a single dosage form will generally be those amounts of the compounds which produce a therapeutic effect. Generally, out of one hundred percent, this amount will range from about 0.1 percent to about ninety-nine percent of active ingredients, from about 5 percent to about 70 percent, or from about 10 percent to about 30 percent.

In certain embodiments, a formulation of the invention comprises an excipient selected from the group consisting of cyclodextrins, celluloses, liposomes, micelle forming agents, e.g., bile acids, and polymeric carriers, e.g., polyesters and polyanhydrides. In certain embodiments, an aforementioned formulation renders orally bioavailable a composition of the invention.

Methods of preparing these formulations or compositions include the step of bringing into association two or more active compounds with the carrier and, optionally, one or more accessory ingredients. In general, the formulations are prepared by uniformly and intimately bringing into association one or more active compounds with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredients. A composition of the invention may also be administered as a bolus, electuary or paste.

In solid dosage forms of the invention for oral administration (capsules, tablets, pills, dragees, powders, granules, trouches and the like), the active ingredients are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredients therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredients only in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compositions of the invention include pharmaceutically acceptable emulsions, microemulsions, solutions, suspensions, syrups and elixirs. In addition to the active ingredients, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredients of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the invention which are suitable for vaginal administration also include pessaries, tampons, creams, gels, pastes, foams or spray formulations containing such carriers as are known in the art to be appropriate.

Dosage forms for the topical or transdermal administration of a composition of this invention include powders, sprays, ointments, pastes, creams, lotions, gels, solutions, patches and inhalants. The active compounds may be mixed under sterile conditions with a pharmaceutically-acceptable carrier, and with any preservatives, buffers, or propellants which may be required.

The ointments, pastes, creams and gels may contain, in addition to the active compounds, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active compounds, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the active compounds to the body. Such dosage forms can be made by dissolving or dispersing the active compounds in the proper medium. Absorption enhancers can also be used to increase the flux of the compounds across the skin. The rate of such flux can be controlled by either providing a rate controlling membrane or dispersing the compounds in a polymer matrix or gel.

Pharmaceutical compositions of this invention suitable for parenteral administration comprise two or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the product of coating materials, such as lecithin, by the maintenance of the required particle size in the case of dispersions, and by the product of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The compositions comprising the two or more therapeutic agents can be, alone or in combination with other therapeutic agents, employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For parenteral application, particularly suitable are oily or aqueous solutions, as well as suspensions, emulsions, or implants, including suppositories. Ampoules are convenient unit dosages. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredients are mixed with an inert diluent.

Aqueous suspensions contain the above-identified combinations of drugs and that mixture has one or more excipients suitable as suspending agents, for example pharmaceutically acceptable synthetic gums such as hydroxypropylmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed. Injectable suspensions may also be prepared, in which case appropriate liquid carriers, suspending agents and the like may be employed. It is also possible to freeze-dry the active compounds and use the obtained lyophilized compounds, for example, for the preparation of products for injection.

In certain embodiments, a combination therapy is considered for use in the methods of the invention. One aspect of combination therapy pertains to a method for providing effective therapeutic treatment in humans, comprising administering an effective or sub-therapeutic amount of one or more therapeutic agent(s); and administering the remaining therapeutic agent(s) in an amount effective to augment the therapeutic effect provided by said one or more therapeutic agent(s). The therapeutic agents can be administered simultaneously or at different times, as long as the dosing intervals (or the therapeutic effects) of the therapeutic agents overlaps. In other words, according to the method of the invention, in certain embodiments the therapeutic agents need not be administered in the same dosage form or even by the same route of administration as each other. Rather, the method is directed to the surprising synergistic and/or additive benefits obtained in humans, when therapeutically effective levels of one or more therapeutic agent(s) have been administered to a human, and, prior to or during the dosage interval for the therapeutic agent(s) or while the human is experiencing the therapeutic effect, an effective amount of other therapeutic agent(s) to augment the therapeutic effect of the original one or more therapeutic agent(s) is administered.

Another aspect of combination therapy relates to an oral solid dosage form comprising a therapeutically effective amount of one or more therapeutic agent(s) together with an amount of the remaining therapeutic agent(s) or pharmaceutically acceptable salt thereof which augments the effect of the one or more therapeutic agent(s).

In certain embodiments, the combination therapy involves co-administering any of the compounds described herein with a glucocorticoid, such as betamethasone, in order to accelerate fetal lung maturity.

In certain embodiments, the combination therapy involves co-administering any of the compounds described herein with an antibiotic.

In some cases, in order to prolong the effect of a drug, it is desirable to slow the absorption of the drug from subcutaneous or intramuscular injection. This may be accomplished by the product of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drugs to polymer, and the nature of the particular polymer employed, the rate of drug release can be controlled. Examples of other biodegradable polymers include poly(orthoesters) and poly(anhydrides). Depot injectable formulations are also prepared by entrapping the drugs in liposomes or microemulsions which are compatible with body tissue.

The preparations of the invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of an active ingredient which is effective to achieve the desired therapeutic response for a particular patient, composition, and mode of administration, without being toxic to the patient.

The selected dosage level will depend upon a variety of factors including the activity of the particular compound of the invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the active compounds employed in the pharmaceutical composition at levels lower than that required in order to achieve the desired therapeutic effect and gradually increase the dosage until the desired effect is achieved.

While it is possible for an active compound of the invention to be administered alone, in certain embodiments the compound is administered as a pharmaceutical formulation (composition).

In another aspect, the invention provides pharmaceutically acceptable compositions which comprise a therapeutically-effective amount of the active compound, as described above, formulated together with one or more pharmaceutically acceptable carriers (additives) and/or diluents. As described in detail below, the pharmaceutical compositions of the invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equities, cattle, swine and sheep; and pets in general.

The compounds of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutic effects of the first administered one is not entirely disappeared when the subsequent is administered.

Micelles

Microemulsification technology improves the bioavailability of some lipophilic (water insoluble) pharmaceutical agents. Examples include Trimetrine (Dordunoo, S. K. et al., Drug Development and Industrial Pharmacy, 17(12), 1685-1713, 1991 and REV 5901 (Sheen, P. C. et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the invention and at least one amphiphilic carrier, in which the micelles have an average diameter of less than about 100 nm. Certain embodiments provide micelles having an average diameter less than about 50 nm, and certain embodiments provide micelles having an average diameter less than about 30 nm, or even less than about 20 nm.

While all suitable amphiphilic carriers are contemplated, in certain embodiments, the carriers are generally those that have Generally-Recognized-as-Safe (GRAS) status, and that can both solubilize the compound of the invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolide fatty glycerides and polyethylene glycols.

In certain embodiments, amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids. In certain embodiments, the fatty acid composition includes capric acid 4-10, capric acid 3-9, lauric acid 40-30, myristic acid 14-24, palmitic acid 4-14, or stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurale and di-laurate, Lecithin, Polysorbate 80, etc. (produced and distributed by a number of companies in USA and worldwide).

Polymers

Hydrophilic polymers suitable for use in the invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. In certain embodiments, the polymers are those having a molecular weight of from about 100 or 120 daltons up to about 5,000 or 10,000 daltons, or about 300 daltons to about 5,000 daltons. In certain embodiments, the polymer is polyethyleneglycol having a molecular weight of from about 100 to about 5,000 daltons, or having a molecular weight of from about 300 to about 3,000 daltons. In certain embodiments, the polymer is polyethyleneglycol of 750 daltons (PEG(750)). Polymers may also be defined by the number of monomers therein; in certain embodiments of the invention utilizes polymers of at least about three monomers, such PEG polymers consisting of three monomers (approximately 150 daltons).

Other hydrophilic polymers which may be suitable for use in the invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and copolymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter $\alpha$, $\beta$, or $\gamma$, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I) et al. (U.S. Pat. No. 3,453,259; incorporated by reference) and Gramera et al. (U.S. Pat. No. 3,459,731; incorporated by reference) described electroneutral cyclodextrins. Other derivatives include cyclodextrins with cationic properties [Parmeter (II), U.S. Pat. No. 3,453,257; incorporated by reference], insoluble crosslinked cyclodextrins (Solms, U.S. Pat. No. 3,420,788; incorporated by reference), and cyclodextrins with anionic properties [Parmeter (III), U.S. Pat. No. 3,426,011; incorporated by reference]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella et al. (U.S. Pat. No. 5,134,127; incorporated by reference).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several non-concentric membranes, i.e., several smaller vesicles contained within a larger vesicle, are termed multi vesicular vesicles.

One aspect of the invention relates to formulations comprising liposomes containing one or more of the therapeutic agents of the invention, where the liposome membrane is formulated to provide a liposome with increased carrying capacity. Alternatively or in addition, the one or more therapeutic agents may be contained within, or adsorbed onto, the liposome bilayer of the liposome. One or more therapeutic agents may be aggregated with a lipid surfactant and carried within the liposome's internal space; in these cases, the liposome membrane is formulated to resist the disruptive effects of the active agent-surfactant aggregate.

According to one embodiment of the invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the invention are in solubilized form. Aggregates of surfactant and active agent (such as emulsions or micelles containing the active agent of interest) may be entrapped within the interior space of liposomes according to the invention. A surfactant acts to disperse and solubilize the active agents, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. In certain embodiments, the surfactants have CMCs in the micromolar range; higher CMC surfactants may be utilized to prepare micelles entrapped within liposomes of the invention, however, micelle surfactant monomers could affect liposome bilayer stability and would be a factor in designing a liposome of a desired stability.

Liposomes according to the invention may be prepared by any of a variety of techniques that are known in the art. See, e.g., U.S. Pat. No. 4,235,871; incorporated by reference; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, one or more active agents are first dispersed by sonication in a lysophosphatidylcholine or other low CMC surfactant (including polymer grafted lipids) that readily solubilizes hydrophobic molecules. The resulting micellar suspension of one or more active agents is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988; incorporated by reference).

Release Modifiers

The release characteristics of a formulation of the invention depend on the encapsulating material, the concentration of encapsulated drugs, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore-forming agents which add microstructure to the matrices (i.e., water soluble compounds, such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups, such as cyanoacrylates and methacrylates).

Immediate/Sustained Release Dosage Forms

The pharmaceutical composition may be formulated in an immediate release dosage form or a sustained release dosage form. In certain embodiments, the invention relates to immediate release dosage forms. An immediate release dosage form may be formulated as a tablet or multiparticulate which may be encapsulated. Other immediate release dosage forms known in the art can be employed. In certain embodiments, the therapeutic agent may be formulated to provide for an increased duration (sustained release) of therapeutic action. These formulations, at comparable daily dosages of conventional immediate release drug, are often associated with a lower incidence or severity of adverse drug reactions; and they can also be administered at a lower daily dose than conventional oral medication while maintaining therapeutic activity.

In certain embodiments, the pharmaceutical composition can be formulated to deliver the therapeutic agent on a predetermined time schedules. In certain embodiments, the therapeutic agent is administered via an oral solid dosage form that includes a sustained release carrier causing the sustained release of any one or more of the therapeutic agent(s) when the dosage form contacts gastrointestinal fluid. The sustained release dosage form may comprise a plurality of substrates which include the drugs. The substrates may comprise matrix spheroids or may comprise inert pharmaceutically acceptable beads which are coated with the drugs. The coated beads may then be overcoated with a sustained release coating comprising the sustained release carrier. The matrix spheroid may include the sustained release carrier in the matrix itself; or the matrix may comprise a normal release matrix containing the drugs, the matrix having a coating applied thereon which comprises the sustained release carrier. In other embodiments, the oral solid dosage form comprises a tablet core containing the drug within a normal release matrix, with the tablet core being coated with a sustained release coating comprising the sustained release carrier. In further embodiments, the tablet contains the drug within a sustained release matrix comprising the sustained release carrier. In additional embodiments, the tablet contains one or more therapeutic agent(s) within a sustained release matrix and remaining therapeutic agent(s) coated into the tablet as an immediate release layer.

The term "sustained release" is defined for purposes of the invention as the release of the therapeutic agent from the formulation at such a rate that blood (e.g., plasma) concentrations (levels) are maintained within the therapeutic range (above the minimum effective analgesic concentration or "MEAC") but below toxic levels over a period of time of about 12 hours or longer.

The therapeutic agents can be formulated as a controlled or sustained release oral formulation in any suitable tablet, coated tablet or multiparticulate formulation known to those skilled in the art. The sustained release dosage form may optionally include a sustained released carrier which is incorporated into a matrix along with the active agents, or which is applied as a sustained release coating.

The sustained release dosage form may include one or more therapeutic agent in sustained release form and the remaining therapeutic agent(s) in the sustained release form or in immediate release form. One or more therapeutic agents may be incorporated into the sustained release matrix along with another therapeutic agent; one or more therapeutic agent may be incorporated into the sustained release coating; incorporated as a separated sustained release layer or immediate release layer; or may be incorporated as a powder, granulation, etc., in a gelatin capsule with the substrates of the invention. Alternatively, the sustained release dosage form may have one or more therapeutic agent in the sustained release form and the remaining therapeutic agent(s) in the sustained release form or immediate release form.

An oral dosage form according to the invention may be provided as, for example, granules, spheroids, beads, pellets (hereinafter collectively referred to as "multiparticulates") and/or particles. An amount of the multiparticulates which is effective to provide the desired dose of the therapeutic agents over time may be placed in a capsule or may be incorporated in any other suitable oral solid form. In one certain embodiments of the invention, the sustained release dosage form comprises such particles containing or comprising one or more active ingredients, wherein the particles have diameter from about 0.1 mm to about 2.5 mm, or from about 0.5 mm to about 2 mm.

In certain embodiments, the particles comprise normal release matrixes containing one or more therapeutic agent with the remaining therapeutic agent(s). These particles are then coated with the sustained release carrier in embodiments where one or more therapeutic agent is immediately released, one or more therapeutic agent may be included in separate normal release matrix particles, or may be co-administered in a different immediate release composition which is either enveloped within a gelatin capsule or is administered separately. In other embodiments, the particles comprise inert beads which are coated with the remaining therapeutic agent(s) with one or more therapeutic agent. Thereafter, a coating comprising the sustained release carrier is applied onto the beads as an overcoat.

The particles may be film coated with a material that permits release of the active agent at a sustained rate in an aqueous medium. The film coat is chosen so as to achieve, in combination with the other stated properties, a desired in vitro release rate. The sustained release coating formulations of the invention should be capable of producing a strong, continuous film that is smooth and elegant, capable of supporting pigments and other coating additives, non-toxic, inert, and tack-free.

Coatings

The dosage forms of the invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release any of the active agent(s) in the desired areas of the gastro-intestinal (GI) tract, e.g., the stomach or small intestine, such that an absorption profile is provided which is capable of providing at least about twelve hours or up to twenty-four hours of therapeutic benefit to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine. In certain embodiments, one or more therapeutic agent(s) is released in one area of the GI tract and the remaining therapeutic agent(s) is released in a second area of the GI tract. In certain embodiments, the therapeutic agents are released in nearly equal amounts at the same location in the GI tract.

Formulations according to the invention that utilize pH-dependent coatings to obtain formulations may also impart a repeat-action effect whereby unprotected drug is coated over an enteric coat and is released in the stomach, while the remainder, being protected by the enteric coating, is released further down the gastrointestinal tract. Coatings which are pH-dependent may be used in accordance with the invention include shellac, cellulose acetate phthalate (CAP), polyvinyl acetate phthalate (PVAP), hydroxypropylmethylcellulose phthalate, and methacrylic acid ester copolymers, zein, and the like.

In certain embodiments, the substrate (e.g., tablet core bead, matrix particle) containing one or more therapeutic agent(s) is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Such formulations are described, e.g., in detail in U.S. Pat. Nos. 5,273,760 and 5,286,493; both incorporated by reference. Other examples of sustained release formulations and coatings which may be used in accordance with the invention include U.S. Pat. Nos. 5,324,351; 5,356,467, and 5,472,712; all incorporated by reference.

Alkylcellulose Polymers

Cellulosic materials and polymers, including alkylcelluloses, provide hydrophobic materials well suited for coating the formulations according to the invention. Simply by way of example, one alkylcellulosic polymer is ethylcellulose, although the artisan will appreciate that other cellulose or alkylcellulose polymers may be readily employed, singly or in any combination, as all or part of a hydrophobic coating.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other embodiments of the invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain embodiments, the acrylic polymer is comprised of one or more ammonio methacrylate copolymers. Ammonio methacrylate copolymers are well known in the art, and are copolymers of acrylic and methacrylic acid esters with a low content of quaternary ammonium groups. In order to obtain a desirable dissolution profile, it may be necessary to incorporate in a coating two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the invention. For example, there are a family of copolymers synthesized from diethylaminoethyl methacrylate and other neutral methacrylic esters, also known as methacrylic acid copolymer or polymeric methacrylates, commercially available as Eudragit® from Rohm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, a plasticizer may be incorporated into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be property determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate can be a plasticizer for the aqueous dispersions of ethyl cellulose of the invention.

Examples of suitable plasticizers for the acrylic polymers of the invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate can be a plasticizer for the aqueous dispersions of ethyl cellulose of the invention.

It has further been found that the addition of a small amount of talc reduces the tendency of the aqueous dispersion to stick during processing, and acts as a polishing agent.

Processes for Preparing Coated Beads

When the aqueous dispersion of hydrophobic material is used to coat inert pharmaceutical beads such as nu panel 18/20 beads, a plurality of the resultant stabilized solid controlled release beads may thereafter be placed in a gelatin capsule in an amount sufficient to provide an effective controlled release dose when ingested and contacted by an environmental fluid, e.g., gastric fluid or dissolution media.

The stabilized controlled release bead formulations of the invention slowly release the therapeutically active agent, e.g., when ingested and exposed to gastric fluids, and then to intestinal fluids. The controlled release profile of the formulations of the invention can be altered, for example, by varying the amount of overcoating with the aqueous dispersion of hydrophobic material, altering the manner in which the plasticizer is added to the aqueous dispersion of hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with one or more therapeutically active agent are prepared, e.g., by dissolving the one or more therapeutically active agent in water and then spraying the solution onto a substrate, for example, nu panel 18/20 beads, using a Wuster insert. Optionally, additional ingredients are also added prior to coating the beads in order to assist the binding of the active agents to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. The barrier agent may or may not affect the dissolution rate of the final product.

The beads may then be overcoated with an aqueous dispersion of the hydrophobic material. The aqueous dispersion of hydrophobic material may further include an effective amount of plasticizer, e.g., triethyl citrate. Pie-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the invention may contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color may be added to Aquacoat® via the product of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

The plasticized aqueous dispersion of hydrophobic material may be applied onto the substrate comprising the one or more therapeutically active agent by spraying using any suitable spray equipment known in the art. In certain embodiments, a Wurster fluidized-bed system is used in which an air jet, injected from underneath, fluidizes the core material and effects drying while the acrylic polymer coating is sprayed on. A sufficient amount of the aqueous dispersion of hydrophobic material to obtain a predetermined controlled release of said therapeutically active agents when said coated substrate is exposed to aqueous solutions, e.g., gastric fluid, is applied, taking into account the physical characteristics of the therapeutically active agents, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the invention can also include erosion-promoting agents such as starch and gums.

The sustained release coatings of the invention can also include materials useful for making microporous lamina in the environment of use, such as polycarbonates comprised of linear polyesters of carbonic acid in which carbonate groups reoccur in the polymer chain. The release-modifying agent may also comprise a semi-permeable polymer.

In certain embodiments, the release-modifying agent is selected from hydroxypropylmethylcellulose, lactose, metal stearates, and mixtures of any of the foregoing.

The sustained release coatings of the invention may also include an exit means comprising at least one passageway, orifice, or the like. The passageway may be formed by such methods as those disclosed in U.S. Pat. Nos. 3,845,770; 3,916,889; 4,063,064; and 4,088,864; all incorporated by reference. The passageway can have any shape such as round, triangular, square, elliptical, irregular, etc.

Matrix Bead Formulations

In other embodiments of the invention, the controlled release formulation is achieved via a matrix having a controlled release coating as set forth above. The invention may also utilize a controlled release matrix that affords in-vitro dissolution rates of the active agents and that releases the active agents in a pH-dependent or pH-independent manner. The materials suitable for inclusion in a controlled release matrix will depend on the method used to form the matrix.

For example, a matrix, in addition to one or more of the active agents, may include: (1) Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agents and which melts (or softens to the extent necessary to be extruded) may be used in accordance with the invention. (2) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

The hydrophobic material may be selected from the group consisting of alkylcelluloses, acrylic and methacrylic acid polymers and copolymers, shellac, zein, hydrogenated castor oil, hydrogenated vegetable oil, or mixtures thereof. In certain embodiments of the invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Hydrophobic materials are water-insoluble with more or less pronounced hydrophilic and/or hydrophobic trends. Generally, the hydrophobic materials useful in the invention have a melting point from about 30° C. to about 200° C. or from about 45° C. to about 90° C. Specifically, the hydrophobic material may comprise natural or synthetic waxes, fatty alcohols (such as lauryl, myristyl, stearyl, cetyl or cetostearyl alcohol), fatty acids, including but not limited to fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones. Suitable waxes include, for example, beeswax, glycowax, castor wax and carnauba wax. For purposes of the invention, a wax-like substance is defined as any material which is normally solid at room temperature and has a melting point of from about 30° C. to about 100° C.

Suitable hydrophobic materials which may be used in accordance with the invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons may have a melting point of between about 25° C. and about 90° C. Of the long chain hydrocarbon materials, fatty (aliphatic) alcohols may be used in certain embodiments. The oral dosage form may contain up to 60% (by weight) of at least one digestible, long chain hydrocarbon.

In certain instances, a combination of two or more hydrophobic materials is included in the matrix formulations. If an additional hydrophobic material is included, it may be selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, or $C_{14}$-$C_{22}$, aliphatic alcohol and, optionally, at least one polyalkylene glycol. The at least one hydroxyalkyl cellulose may be a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the oral dosage form will be determined, inter alia, by the precise rate of release desired for the therapeutic agent. The at least one aliphatic alcohol may be, for example, lauryl alcohol, myristyl alcohol or stearyl alcohol. In certain embodiments of the oral dosage form, however, the at least one aliphatic alcohol is cetyl alcohol or cetostearyl alcohol. The amount of the at least one aliphatic alcohol in the oral dosage form will be determined, as above, by the precise rate of release desired for the therapeutic agents. It will also depend on whether at least one polyalkylene glycol is in or absent from the oral dosage form. In the absence of at least one polyalkylene glycol, the oral dosage form may contain between 20% and 50% (by wt) of the at least one aliphatic alcohol. When at least one polyalkylene glycol is in the oral dosage form, then the combined weight of the at least one aliphatic alcohol and the at least one polyalkylene glycol may constitute between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a considerable extent, the release rate of the active agent from the formulation. The ratio of the at least one hydroxyalkyl cellulose to the at least one aliphatic alcohol/polyalkylene glycol may be between 1:2 and 1:4, or between 1:3 and 1:4.

The at least one polyalkylene glycol may be, for example, polypropylene glycol or polyethylene glycol. The number average molecular weight of the at least one polyalkylene glycol may be between about 1,000 and about 15,000, or between about 1,500 and about 12,000. Another suitable controlled release matrix would comprise an alkylcellulose (especially ethyl cellulose), a $C_{12}$ to $C_{36}$ aliphatic alcohol and, optionally, a polyalkylene glycol. In certain embodiments, the matrix includes a pharmaceutically acceptable combination of at least two hydrophobic materials. In addition to the above ingredients, a controlled release matrix may also contain suitable quantities of other materials, e.g., diluents, lubricants, binders, granulating aids, colorants, flavorants and glidants that are conventional in the pharmaceutical art.

EXEMPLIFICATION

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Example 1 (Prophetic)—Functional Characterization of Antimuscarinic/Antispasmodic Activity—In Vitro Studies Uterine Smooth Muscle Strips.

Isolated uterus preparations (approximately 6-mm long and 1-mm wide) from rats are contracted with 0.003 µM oxytocin and the contractions are reduced with the test articles and compared to the effects of reference calcium antagonist, such as nifedipine. Contractions can also be induced by carbachol or a high potassium concentration in the bath fluid.

In each experiment up to six strips are suspended in individual tissue chambers and allowed to equilibrate with the bathing solution for at least 30 min before proceeding with the experiment. The inhibition is expressed as $IC_{50}$ or percent.

Carbachol- and Potassium-Induced Contractions.

In order to assess the viability of each tissue and to serve as a frame of reference, contractions of each strip of tissue are recorded initially in response to exposure to tissue medium in which the NaCl Was replaced by KCl to yield a concentration of 137.7 mM KCl in the medium. This is followed by return to the standard medium, and then by exposures to progressively increasing concentrations of carbachol, with separate exposures to each concentration only until the peak response has been recorded. The effects of increasing concentrations of the test article on contractions induced by 137.7 mM KCl are recorded in separate experiments. $IC_{50}$ values or pA2 values or inhibition expressed in percent are calculated using conventional statistic methodology.

Example 2 (Prophetic)—Muscarinic Receptor Binding Test (In Vitro)

a. Preparation of Membranes

From a male Wistar rat (Japan SLC), the heart and submandibular gland are excised, mixed with a 20 mM HEPES buffer (pH 7.5, which will hereinafter be abbreviated as "HEPES buffer") containing 5 times the volume of 100 mM sodium chloride and 10 mM magnesium chloride, followed by homogenization under ice-cooling. The resulting mixture is filtered through gauze, followed by ultracentrifugation at 50,000×g and 4° C. for 10 minutes. The precipitate obtained is suspended in an HEPES buffer, followed by further ultracentrifugation at 50,000×g and 4° C. for 10 minutes. The precipitate obtained is suspended in an HEPES buffer. The resulting suspension was stored at −80° C. and provided for the test after melting upon use.

b. Muscarinic $M_2$ Receptor Binding Test

The test is carried out in accordance with the method of Doods et al. (J. Pharmacol. Exp. Ther., 242, 257-262, 1987) with some modifications. The cardiac membrane sample, [$^3$H]-quinuclidinyl benzilate and the test compound are incubated in a 0.5 mL HEPES buffer at 25° C. for 45 minutes, followed by suction filtration through a glass filter (Whatman GF/B). The filter is washed three times with 5 mL portions of an HEPES buffer. The radioactivity of the [$^3$H]-quinuclidinyl benzilate adsorbed on the filler is measured by a liquid scintillation counter. Incidentally, nonspecific binding of the receptor is determined by the addition of 1 µM atropine. The binding of the test compound for the muscarinic $M_2$ receptor is determined from a dissociation constant (Ki) calculated, in accordance with Chen and Prusoff (Biochem. Pharmacol. 22, 3099, 1973), based on the concentration ($IC_{50}$) of the test compound at which 50% of the binding of the [$^3$H]-quinuclidinyl benzilate, that is, a labeled ligand is inhibited.

c. Muscarinic $M_3$ Receptor Binding Test

In a similar manner to the above muscarinic $M_2$ receptor binding test except that the submandibular gland is used as a membrane sample and [$^3$H]-N-methylscopolamine is used as a labeled ligand, a muscarinic $M_3$ receptor binding test is carried out.

Compounds useful in the described methods have a Ki value of from about $10^{-8}$ to $10^{-10}$ for the $M_3$ receptor, and an affinity for $M_3$ receptor that is at least 10 times as high as that for $M_2$ receptor.

Example 3 (Prophetic)—Muscarinic Receptor Antagonism Test (In Vivo)

a. Test on Rhythmic Bladder Contraction in Rat

A female Wistar rat (130-200 g) is subjected to urethane anesthesia (1.0 g/kg s.c.), followed by ligation of the ureter on the kidney side. A urethral catheter is allowed to remain in the bladder, and about 1.0 mL of physiological saline is injected into the bladder through the catheter to cause rhythmic bladder contraction. Intravesical pressure is measured by a pressure transducer. After rhythmic contraction continues stable for at least 5 minutes, the test compound is cumulatively administered from the external jugular vein. Five to ten minutes later, the intravesical pressure is measured. An inhibition ratio of bladder contraction is determined compared with the bladder contraction before administration of the test compound and the dose of the test compound required for 30% inhibition of the bladder contraction before administration is designated as $ED_{30}$.

b. Test on Salivary Secretion in Rat

A male Wistar rat (160-190 g) is subjected to anesthesia with urethane (0.8 g/kg i.p.), and the test compound is administered (to the control group: solvent). Fifteen minutes later, 0.8 µmol/kg of oxotremorine is administered. In each case, the drug is administered through the femoral artery. The saliva secreted for 5 minutes after the administration of oxotremorine is collected and weighed. The inhibition ratio against the amount of saliva in the control group is determined and the dose of the test compound required for 50% inhibition of the amount of saliva in the control group is designated as $ID_{50}$.

As an example, the $ID_{50}$ value of atropine is substantially the same as the $ED_{30}$ value obtained in the above rat rhythmical bladder contraction test, while the $ID_{50}$ value of a compound useful in the methods describe herein is at least 5 times as much as the above-described $ED_{30}$ value, which suggested that the test compound has relatively weak action against the salivary secretion.

c. Test on Bradycardia in Rat

The test is carried out in accordance with the method of Doods et al. (J. Pharmacol. Exp. Ther., 242, 257-262, 1987).

A male Wistar rat (250-350 g) is subjected to anesthesia with pentobarbital sodium (50 mg/kg i.p.). The neck region is excised, followed by the division of right and left vagus nerves. After a cannula is inserted into a trachea to secure airway, a stainless rod is inserted from the Orbit and the spinal cord is destroyed. Under artificial respiration (at 10 cc/kg and 50 times/minute), the rectal temperature is maintained at 37.5° C. and a heart rate is monitored at the common carotid artery. An indwelling needle is fixed to the femoral artery, from which the drug is administered. After the destruction of the spinal cord, the rat is allowed to stand for 15 minutes to attain the equilibrium, followed by the administration of atenolol (10 mg/kg). After the equilibration for additional 15 minutes, the test compound is administered. Fifteen minutes later, oxotremorine is cumulatively administered, thereby the reduction in the heart rate is measured. The amount of the test compound required for 10-times rightward shift of the dose-response curve of the control group is designated as $DR_{10}$.

As an example, compounds useful in the methods described herein have sufficiently low activity against bradycardia and no bradycardia is observed at the administration amount of several mg/kg.

Example 4 (Prophetic)—Effects on Myometrial Contractions

Time-dated pregnant Wistar rats (Charles River Laboratories, Wilmington, Mass.) between days 13 and 15 of gestation (term, 21 to 23 days) are killed by decapitation. Four strips of myometrium of approximately 1 cm in length and 3 to 4 mm wide (approximately 0.5 mL in volume) are obtained from both uterine horns (2 from each) per animal and dissected free from gestational membranes. The uterine samples then are placed in 10-mL tissue baths containing DeJalon's solution at 32° C. and continuously exposed to a 95% $O_2$, 5% $CO_2$ sweep gas, under a resting tension of 1 g.

Spontaneous muscular activity is recorded by a Grass FT03 force transducer (Grass Corp, Quincy, Mass.) connected to a Grass Model 7 polygraph, calibrated as per manufacturer's instructions. Myometrial samples are allowed to equilibrate for at least 30 minutes, after which, predictable, stable activity can be observed. Samples that do not maintain regular phasic activity after this period are discarded. Once baseline values for amplitude and frequency of contractions are recorded, cumulative doses of a commercially available purified botulinus toxin type A (BTX-A, Botox; Allergan Inc., Irvine, Calif.) are added to the tissue baths, starting at 5 U. Each dose of BTX-A is tested for at least 15 minutes at least 3 times. Myometrial activity data points for each dose are entered as mean percentual variations from the baseline values for both amplitude and frequency of contractions. After data collection for each sample is complete, the tissue bath is completely washed out of the drug, and normal spontaneous activity is allowed to resume. If normal activity cannot be reestablished at that time, the data are considered not valid and re discarded.

As an example, compounds useful in the methods described herein depress both the amplitude and the frequency of myometrial contractions.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method for preventing preterm labor, stopping labor preparatory to Cesarean delivery or controlling the timing of parturition, consisting essentially of the step of administering to a patient in need thereof an effective amount of a muscarinic antagonist, wherein the muscarinic antagonist is oxybutynin.

2. The method of claim 1, wherein the method consists of the step of administering to the patient in need thereof the effective amount of the muscarinic antagonist.

3. The method of claim 1, wherein the method delays or prevents preterm labor; and labor is delayed or prevented for at least about 2 days.

4. The method of claim 1, wherein the patient in need thereof is
   a woman pregnant with a fetus at less than 40 weeks gestational age;
   a woman pregnant with a fetus weighing less than about 2500 g;
   a pregnant woman whose cervix is dilated less than about 4 cm;
   a woman pregnant with a fetus who is not suffering from fetal distress;
   a pregnant woman who smokes cigarettes, or smoked cigarettes prior to conception;
   a pregnant woman who was overweight or obese prior to conception, or was underweight prior to conception;
   a pregnant woman with limited access to prenatal care;
   a pregnant woman who drinks alcohol during her pregnancy, or uses illegal drugs during her pregnancy;
   a pregnant woman also suffering from high blood pressure, preeclampsia, diabetes, a blood clotting disorder, placenta previa, placental abruption, cervical insufficiency, or an infection;
   a pregnant woman who has undergone surgical fetal intervention;
   a pregnant woman who will undergo surgical fetal intervention;
   a pregnant woman who is under 17 years of age;
   a pregnant woman who is over 35 years of age;
   a pregnant woman who is African American;
   a pregnant woman who suffered from vaginal bleeding during the first or second trimester of her pregnancy;
   a pregnant woman who suffered from anemia during the first or second trimester of her pregnancy;
   a pregnant woman who suffers from stress;
   a pregnant woman who suffers from polyhydramnios;
   a pregnant woman who conceived via in vitro fertilization;
   a pregnant woman who is pregnant with twins or other multiples;
   a pregnant woman who has a family history or a personal history of premature labor,
   a pregnant woman who conceived less than 14 months after giving birth to a previous child; or
   a pregnant woman who is not also suffering from urinary incontinence.

* * * * *